United States Patent
Fehling et al.

(10) Patent No.: US 9,402,614 B2
(45) Date of Patent: Aug. 2, 2016

(54) SPREADER FOR THE ATRIUM OF THE HEART

(71) Applicant: Fehling Medical Corporation, Acworth, GA (US)

(72) Inventors: Guido Fehling, Karlstein (DE); Ingo Kutschka, Hannover (DE)

(73) Assignee: FEHLING MEDICAL CORPORATION, Acworth, GA (US)

( * ) Notice: Subject to any disclaimer, the term of this patent is extended or adjusted under 35 U.S.C. 154(b) by 0 days.

(21) Appl. No.: 14/226,209

(22) Filed: Mar. 26, 2014

(65) Prior Publication Data

US 2014/0296649 A1 Oct. 2, 2014

(30) Foreign Application Priority Data

Mar. 27, 2013 (DE) .......................... 10 2013 205 519

(51) Int. Cl.
- *A61B 1/32* (2006.01)
- *A61B 17/02* (2006.01)
- *A61F 2/24* (2006.01)

(52) U.S. Cl.
CPC ......... *A61B 17/0293* (2013.01); *A61B 17/0218* (2013.01); *A61F 2/2487* (2013.01); *A61B 2017/0225* (2013.01)

(58) Field of Classification Search
CPC ............... A61B 2017/0225; A61B 2017/0237; A61B 17/0218; A61F 2/2487
See application file for complete search history.

(56) References Cited

U.S. PATENT DOCUMENTS

| 4,984,564 | A  | * | 1/1991  | Yuen ............................. 600/207 |
| 5,139,511 | A  | * | 8/1992  | Gill et al. ...................... 606/198 |
| 6,524,320 | B2 | * | 2/2003  | DiPoto .......................... 606/108 |
| 7,871,374 | B2 |   | 1/2011  | De Canniere et al. |
| D664,651  | S  | * | 7/2012  | Hermle ......................... D24/135 |
| D664,652  | S  | * | 7/2012  | Hermle ......................... D24/135 |
| 8,388,525 | B2 | * | 3/2013  | Poo et al. ...................... 600/206 |
| 8,460,185 | B2 |   | 6/2013  | Epstein et al. |
| 8,721,538 | B2 | * | 5/2014  | Bucholz ........................ 600/208 |
| 2006/0052802 | A1 | * | 3/2006  | Sterman et al. ................ 606/148 |
| 2007/0038032 | A1 |   | 2/2007  | De Canniere et al. |
| 2007/0225801 | A1 |   | 9/2007  | Drews et al. |
| 2008/0058604 | A1 | * | 3/2008  | Sorensen ...................... 600/208 |
| 2008/0058605 | A1 | * | 3/2008  | Sorensen ...................... 600/208 |
| 2009/0299147 | A1 | * | 12/2009 | Epstein et al. ................ 600/213 |
| 2010/0249519 | A1 | * | 9/2010  | Park et al. ..................... 600/206 |
| 2011/0022165 | A1 |   | 1/2011  | Oba et al. |
| 2011/0071622 | A1 |   | 3/2011  | Fehling et al. |
| 2011/0137128 | A1 | * | 6/2011  | Poo et al. ...................... 600/206 |

(Continued)

FOREIGN PATENT DOCUMENTS

| DE | 202012101617 | 5/2012 |
| DE | 102012201983 | 8/2013 |

(Continued)

*Primary Examiner* — Jacqueline Johanas (74) *Attorney, Agent, or Firm* — Akerman LLP; Peter A. Chiabotti (57) ABSTRACT

A spreader for the atrium of the heart is disclosed, particularly for the exposure of the mitral valve, having a thin-walled axially continuous hollow retractor body, the diameter of which expands from a distal edge to a proximal edge. The wall of the retractor body is made of an elastically deformable flat material, preferably of a shape memory metal. At the proximal edge of the retractor body, a receptacle is arranged, into which a fixing rod for positioning and fixing the retractor body can be inserted.

8 Claims, 9 Drawing Sheets

(56) References Cited

U.S. PATENT DOCUMENTS

| | | |
|---|---|---|
| 2011/0237903 A1 | 9/2011 | Fehling et al. |
| 2012/0029272 A1* | 2/2012 | Shelton et al. .................. 600/37 |
| 2013/0066157 A1* | 3/2013 | Guralnik et al. .............. 600/204 |
| 2014/0277384 A1* | 9/2014 | Melsheimer ................. 623/1.18 |

FOREIGN PATENT DOCUMENTS

| | | |
|---|---|---|
| DE | 102012107521 | 2/2014 |
| WO | 2008098616 | 8/2008 |

* cited by examiner

SPREADER FOR THE ATRIUM OF THE HEART

CROSS REFERENCE TO RELATED APPLICATIONS

This application claims priority to German Patent Application No. DE 10 2013 205 519.6 filed Mar. 27, 2013, which is hereby incorporated by reference in its entirety.

BACKGROUND

This application relates to a spreader for the atrium of the heart.

In heart surgery, minimally invasive surgical techniques have become increasingly common. In particular, in the surgical treatment of the mitral valve and the tricuspid valve, minimally invasive surgical procedures play an important role. In these procedures, the surgeon accesses the heart by way of a small anterolateral incision of a few centimeters between the ribs without opening the sternum. A rib spreader, also referred to as rib retractor, keeps the ribs apart in order to keep an access to the heart open.

In surgeries of the cardiac valve, particularly in the frequent surgery of the mitral valve, first the atrium is opened up, the left atrium in mitral valve surgery. In order to maintain unobstructed view of, and access through the atrium to the mitral valve for the surgeon, spreaders, also referred to as retractors, which hold the atrial roof and the surrounding soft tissue back, are used in order to expose the mitral valve for the surgical procedure.

Such spreaders can be conventional wound hooks, wherein several wound hooks each having a rod-shaped handle are used. From WO 2008/098616 A1 it is known to use a retractor instead of individual separate wound hooks, which at the distal end of a rod carries a sheet-shaped clamp, to which a second blade is articulated in a pivotable manner. The retractor is introduced into the opened atrium with its blades folded, whereupon the two blades of the clamp are opened up so that they are approximately at a right angle to one another. The two blades of the clamp make it possible to both elevate the atrial roof and also to hold the soft tissue back in a caudal direction. However, the two blades positioned at a right angle to one another only bring about a spreading and holding back of half of the circumference of the field of vision, and of the instrument access to the mitral valve.

From US 2007/0038032 A1, a spreader from the atrium of the heart is known, wherein an elastic flat material is bent into a hollow retractor body, the diameter of which increases from a distal edge to a proximal edge. The retractor body is provided with an open slot extending axially in a surface line. The longitudinal edges facing one another and delimiting the gap can be pushed together, against one another and overlapping one another, against the elasticity of the material, as a result of which the retractor body assumes a cylindrical shape having a smaller diameter. In this rolled-up form with a small diameter, the retractor body can be introduced into the opened atrium. If the retractor body is then released, it expands into its funnel-shaped form in order to spread the tissue and to keep the operating field open. At the distal edge, the overlapping longitudinal edges of the retractor body are held together by way of a button-hole connection. The proximal edge can be held together by way of two rods, or by a clamp. The purpose of the rods, that is, the clamp, is to insert the retractor body into the atrium and will have to be removed after the insertion in order not to obstruct the view and the surgical process. After removal of the rods, that is, the clamp, the retractor body is therefore unsecured in its position in the atrium.

SUMMARY

The object is to provide a spreader, that is, a retractor, which is easy to handle, which keeps the view of and instrument access to the mitral valve open in the best manner possible, and which can be reliably fixed in its optimal position during the surgery.

This objective is achieved by a spreader having the features and structures recited herein.

The spreader is provided with a retractor body having the shape of a thin-walled cone or funnel, that is, the diameter thereof continuously increases from a more narrow open distal edge to a wider open proximal edge. The wall of the retractor body is made of a flat material, which can be elastically deformed from its stress-free initial form. In a surface line, the wall is divided by an axially extending gap. Thus, it is possible to compress the retractor body against the elastic restoring force of its wall to a smaller diameter, wherein the retractor body elastically spreads back to its initial form when force is no longer applied to the wall.

Basically, any flat material having sufficient stability and elastic deformability can be used for the wall. Preferably, the retractor body is produced of a metal sheet with suitable elasticity. Particularly suitable is a sheet of a shape memory metal, for example, a nickel-titanium alloy, which makes a pseudo-elastic, that is, a superelastic deformation possible.

Preferably, the wall of the retractor body can be provided with a plurality of apertures so that a grid-shaped structure is formed. This makes material savings and a defining of the elasticity behavior possible.

At the proximal edge of the retractor body, a first receptacle is arranged, in which a fixing rod can be releasably inserted. The first receptacle is configured such that the fixing rod inserted therein is pivotably connected to the retractor body. Due to the pivotable connection, the angle between the fixing rod and the center axis of the retractor body can be adjusted.

In order to insert the retractor body into the atrium of the heart, in one embodiment, a second receptacle can be arranged at the proximal edge of the retractor body, into which a guide rod can be releasably inserted. The second receptacle is thereby configured such that the guide rod inserted therein is rigidly connected to the retractor body. In this embodiment, the fixing rod and the guide rod can be inserted into the respective receptacles, wherein the free longitudinal edges of the wall of the retractor body are moved in a peripheral direction against each other, and optionally, overlappingly superimposed upon each other, by means of the two rods in order to reduce the diameter of the retractor body for insertion into the atrium. After insertion of the retractor body, the guide rod and the fixing rod are released from their respective receptacle so that the retractor body is freely seated in the atrium of the heart.

In a second embodiment, the free longitudinal edges of the wall of the retractor body are moved extracorporeally by hand one above the other in order to reduce the diameter of the retractor body. The overlapping longitudinal edges are gripped and held together by a clamp. The clamp also serves the purpose of inserting the retractor body into the atrium of the heart, and in particular, to position it at the annulus of the mitral valve.

Once the retractor body is inserted by means of the guide rod or by means of the clamp, the guide rod and the fixing rod, that is, the clamp are removed so that the retractor body elastically expands thus spreading the surrounding tissue. Subsequently, the fixing rod is introduced and inserted into the first receptacle by way of an additional small incision laterally next to the intercostal access, through which the retractor body is inserted. By way of the fixing rod, which is pivotably connected to the retractor body via the receptacle, the retractor body can now be optimally adjusted in its position, and can be fixed in this optimal position. Since the fixing rod is thereby guided laterally through the thorax wall outside at the proximal edge of the retractor body, the fixing rod does not obstruct the free view and the instrument access to the operating field. Therefore, the fixing rod can remain on the retractor body during the entire surgery in order to reliably fix it in its optimal position.

In a preferred embodiment, guides for receiving threads are arranged at the distal edge and the proximal edge, respectively. The threads are fastened in the tissue, preferably in the area of the annulus of the mitral valve, and are placed into the guides such that they extend from the respective distal guide adjacent to the inside of the wall of the retractor body to the corresponding proximal guide, and from there on can be guided extracorporeally. Thus, it is possible to position and hold the spreader optimally on the mitral valve by way of these threads.

The disclosure is described in more detail with the aid of exemplary embodiments illustrated in the drawings below:

DETAILED DESCRIPTION OF THE ILLUSTRATED EMBODIMENTS

The spreader according to the disclosure, also referred to as retractor, is shown in the illustrated exemplary embodiment for the exposure of the mitral valve of the heart during a minimally invasive operation. Most frequently, such an operation is for the reconstruction of the mitral valve. An analogous spreader can also be used for the minimally invasive operation of the tricuspid valve.

Figure 1:
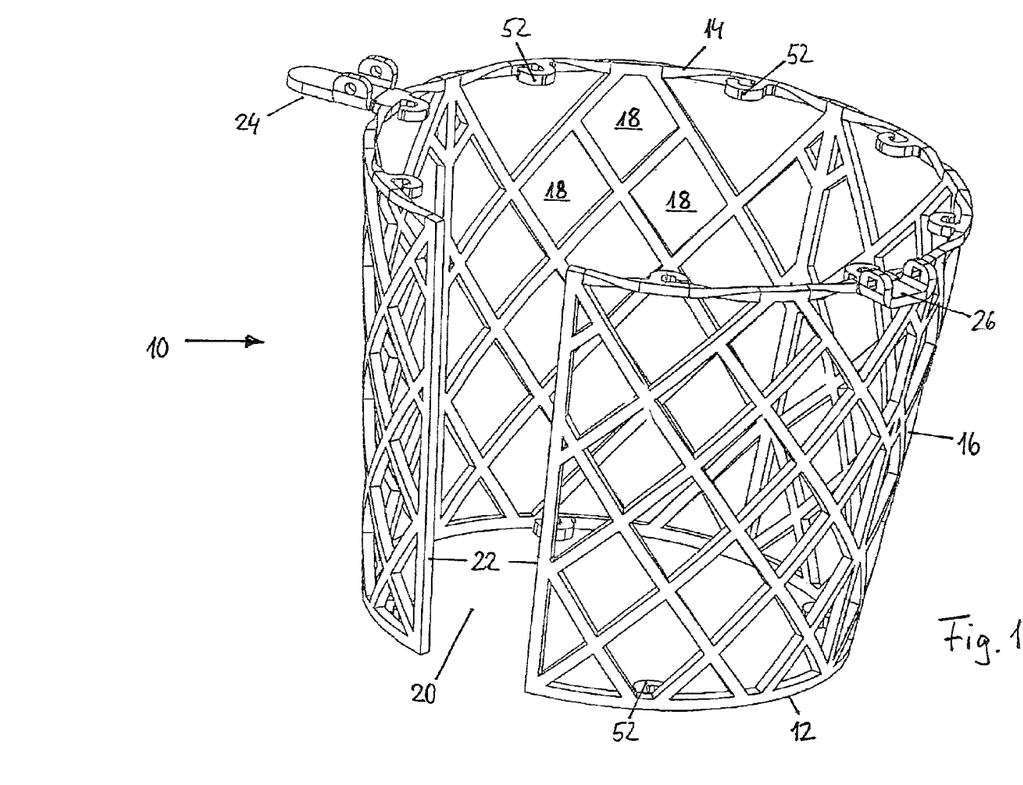
FIG. 1 is a perspective view of the retractor body of the spreader.

In a first embodiment, the spreader is provided with a retractor body 10 as shown in FIG. 1, which is inserted via an intercostal access into the opened up left atrium. The retractor body 10 has the form of a thin-walled, continuously hollow cone, the diameter of which increases from a distal lower edge 12 to a proximal upper edge 14. In the illustrated exemplary embodiment, the retractor body 10 has the shape of a straight truncated circular cone. Other configurations are likewise possible, for example, the retractor body 10 can have the shape of an oval cone, or a conical shape having a surface line that is not straight. The crucial factor is that the retractor body 10 continuously expands from the more narrow distal edge 12 to the wider proximal edge 14.

Figure 2:
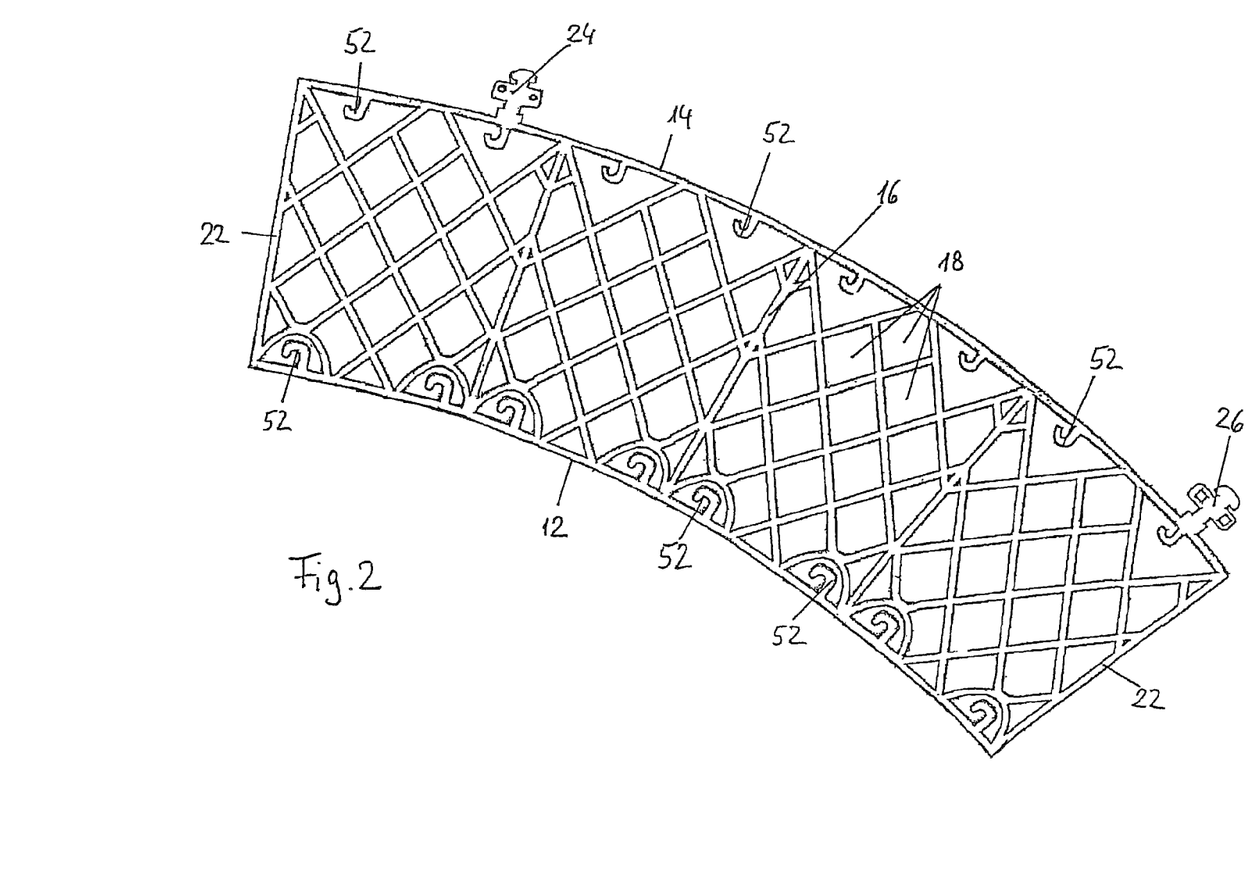
FIG. 2 shows a stamped part for producing the retractor body.

The wall 16 of the retractor body is made of an elastically deformable flat material, preferably of a metal sheet, and particularly of a form memory metal, for example, of a nickel-titanium alloy. The wall 16 is produced from the flat material, for example, the metal sheet, as a stamped part, as illustrated in FIG. 2. In order to save on material and weight, the wall 16 is preferably configured with a plurality of apertures 18, which are arranged in a grid pattern so that a grid-shaped structure of the wall 16 is formed. The stamped part shown in FIG. 2 is re-formed into the conical shape of the retractor body as shown in FIG. 1. In this conical shape, the wall 16 remains inherently stable but elastically deformable. In this basic shape shown in FIG. 1, the wall 16 of the retractor body 10 is axially continuous split in a surface line. Thus, the retractor body 10 is provided with a continuous gap 20 in its shell, the width of which it about 15° to 45° in a peripheral direction. From its basic shape as shown in FIG. 1, which is stored in the shape memory of the wall 16, for example, the diameter of the retractor body 10 can be reduced by moving the axial longitudinal edges 22 of the gap 20 against each other under elastic deformation of the retractor body 10. This reduction of the diameter can be carried out to the extent that the longitudinal edges 22 touch and the gap 20 is closed. In addition thereto, it is also possible to push the longitudinal edges 22 one above the other in a peripheral direction so as to overlap, so that the diameter of the retractor body 10 is further reduced. If the force bringing about this elastic deformation of the retractor body 10 is no longer applied, the retractor body 10 spreads back to its basic shape with the larger diameter as shown in FIG. 1.

Figure 3:
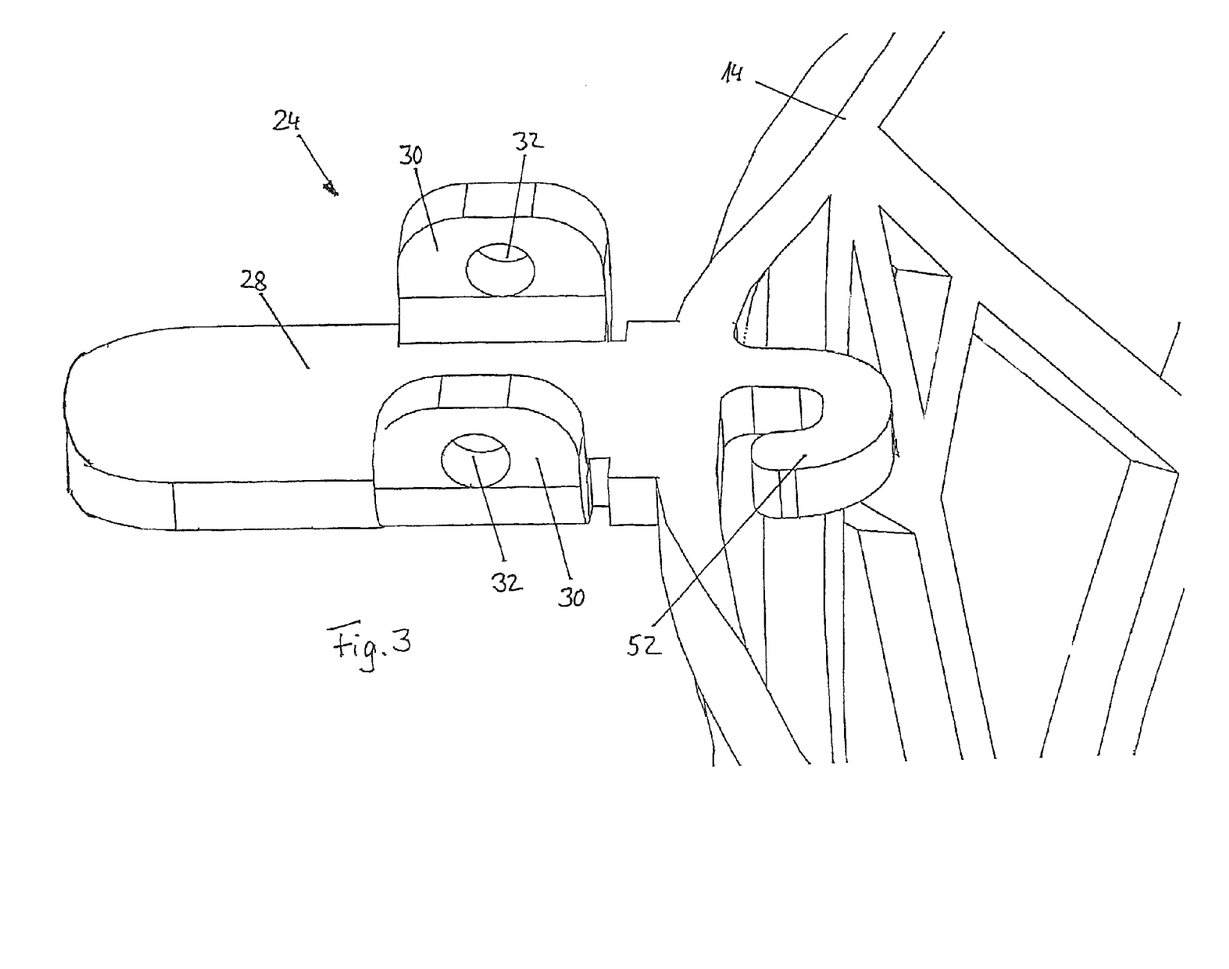
FIG. 3 is an enlarged sectional illustration of a first receptacle for the pivotable connection of a fixing rod to the retractor body.

At the proximal edge 14 of the retractor body 10, two receptacles 24 and 26 are included or molded on. The receptacles 24 and 26 are arranged at an angular distance of about 120° to 180° to one another, wherein the gap 20 is located in this circumferential angular range enclosed between the receptacles 24 and 26. In FIG. 3, the first receptacle 24 is shown in an enlarged sectional illustration, whereas the second receptacle 26 in FIG. 4 is shown in an enlarged cutaway illustration.

Figure 6:
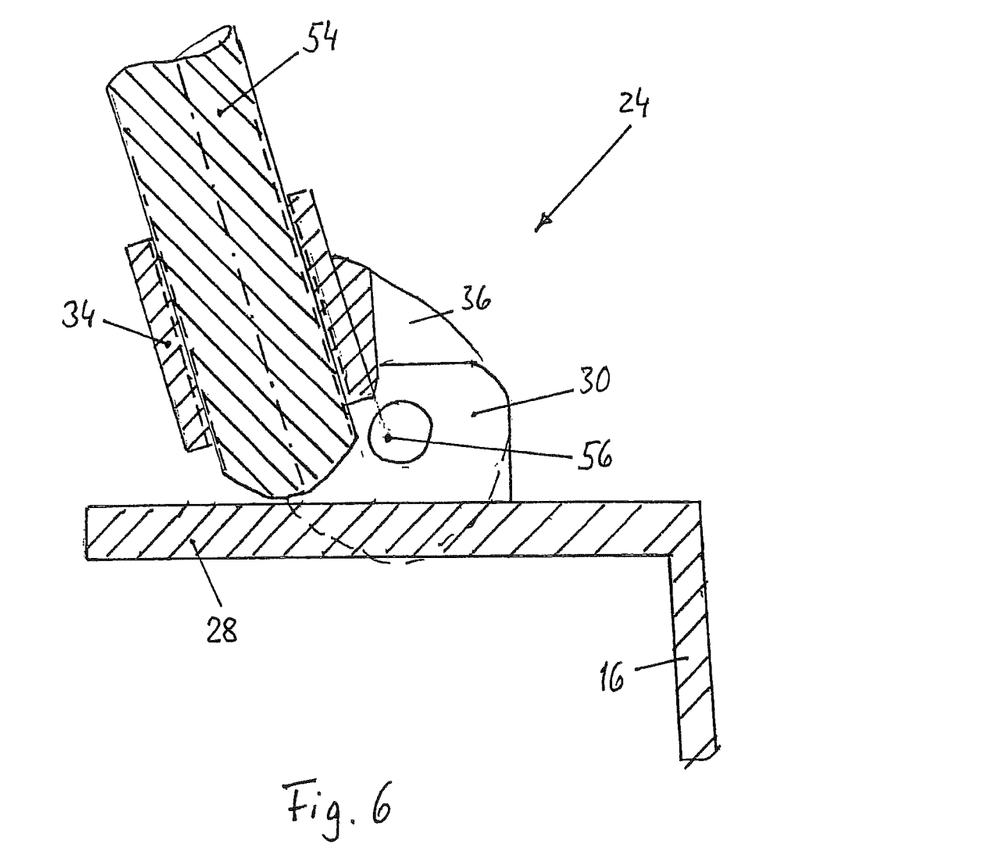
FIG. 6 shows a cross-sectional view of the first receptacle with inserted fixing rod.

The first receptacle 24 comprises a tap 28 molded to the wall 16, which is bent at right angles to the outside after the wall 16 has been stamped out. To both sides of the tab 28, flanges 30 are molded, which also are bent in the proximal direction at right angles from the tab 28. The two flanges 30 are provided with bearing bores 32 that are axially aligned with one another having an annular cross section. A threaded bushing 34 is inserted into the receptacle 24, which is provided with a continuous bore having an internal thread, into which a fixing rod 54 having a screw thread at its distal end can be screwed, as can be seen in FIG. 6. The threaded bushing 34 is provided with two flanges 36, which are tangential parallel to each other in an interspaced manner, each having annular bearing bores 38 that are axially aligned with one another. The threaded bushing 34 is put onto the receptacle 24 such that the flanges 36 of the threaded bushing 34 encompass the flanges 30 of the receptacle 24 from the outside, wherein the bearing bores 38 of the flanges 36 and the bearing bores 32 of the flanges 30 are axially aligned with one another. An axle pin 56 is inserted into the bearing bores 32 and 38 so that the threaded bushing 34 is pivotably connected to the receptacle 34 around an axis that is tangential with respect to the retractor body 10. By way of the receptacle 24 and the threaded bushing 34, the fixing rod 54 screwed into the threaded bushing 34 can be pivoted in a radial direction with respect to the retractor body 10 in a plane that includes the center axis of the retractor body 10. When pivoting the fixing rod 54 radially towards the outside, the fixing rod 54, with its distal end protruding through the threaded bushing 34, comes to rest on the tab 28 of the first receptacle 24. In this way, the angle between the fixing rod 54 and the center axis of the retractor body 10 are fixed into place. With the retractor body 10 inserted into the heart, the tab 28 is thereby held abutting to the distal end of the fixing rod 54 as a result of the pressure acting on the retractor body 10 by the tissue spread open by the retractor body 10. By screwing the fixing rod 54 into the threaded bushing 34 of the first receptacle 24 in different ways, the angle between the fixing rod 54 and the center axis of the retractor body 10 can thus be adjusted and fixed into place.

Figure 4:
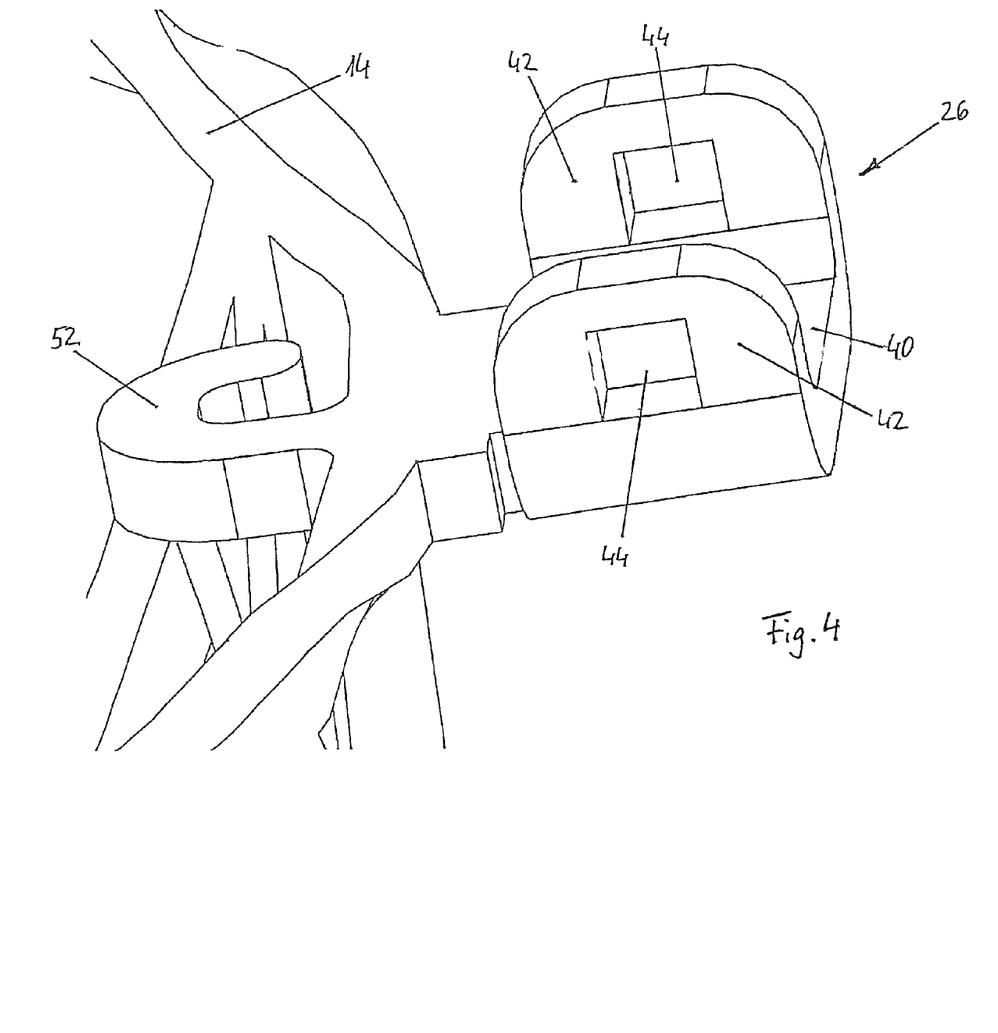
FIG. 4 is an enlarged sectional illustration of a second receptacle for the angle-rigid connection of a guide rod to the retractor body.
Figure 5:
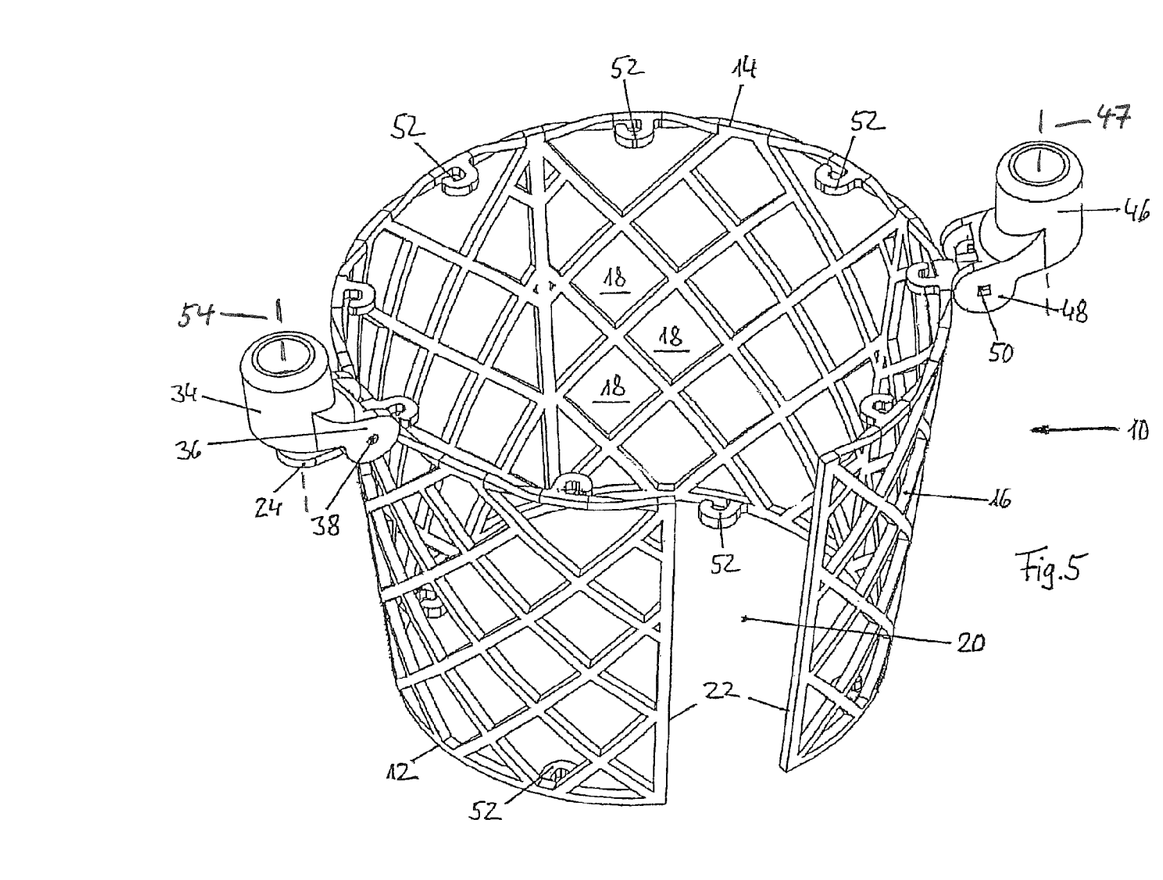
FIG. 5 is a perspective illustration of the retractor body with the receptacles for the rods.

The second receptacle 26 shown in FIG. 4 in an enlarged sectional illustration comprises a tab 40 molded onto the proximal edge 14 of the wall 16 during die-cutting, said flange being bent towards the outside at right angles. On each of the two lateral edges of the tab 40, a flange 42 is bent upwards at right angles. In the two flanges 42, axially aligned bearing apertures 44 are provided having a non-round cross section, for example, a square one. A threaded bushing 46 provided with a threaded bore, into which a fixing rod (not shown) can be screwed by way of a distally formed screw thread, is inserted into the receptacle 26. The threaded bushing 46 is provided with two tangentially protruding flanges 48, which are provided with bearing apertures 50 having the same non-round cross-sectional shape as the bearing apertures 44. The threaded bushing 46 is positioned on the receptacle 26, wherein the flanges 48 of the threaded bushing 46 engage the flanges 42 of the tab 40 from the outside and align the bearing apertures 50 with the bearing apertures 44. Into the bearing apertures 44 and 50 aligned with one another, a bearing pin is inserted having the same non-round, for example, square cross-section as the bearing apertures 44 and 50. Thus, the threaded bushing 46 and as the case may be, the guide rod 47 screwed into same, are connected to the retractor body 10 at a fixed angle and in such a way that it cannot pivot. Preferably, the guide rod 47 extends approximately parallel to the center axis of the retractor body 10.

Furthermore, guides 52 are arranged at the distal edge 12 and at the proximal edge 14 of the retractor body 10. The guides 52 are molded in one piece onto the stamped part of the wall 16 and have the shape of hook-shaped open eyelets, which are bent away from the respective edge 12 and/or edge 14 of the wall 16 at a right angle into the inside of the cone of the retractor body 10. Both at the distal edge 12 and at the proximal edge 14, several guides 52 are arranged, preferably having the same number and angular arrangement at the distal edge 12 and at the proximal edge 14. For the retractor body 10 illustrated in the drawing, eight guides 52 each are provided at the distal edge 12 and at the proximal edge 14, for example. Into the guides 52, threads can be placed such that said threads extend from a guide 52 at the distal edge 12 to a corresponding guide 52 at the proximal edge 14, respectively, wherein they abut the inner side of the wall 16.

The mode of operation and the application of the spreader are described in more detail therebelow on the example of a minimally invasive operation of the mitral valve.

A right-side anterolateral intercostal access is created, wherein the ribs are kept separated by way of a rib spreader. Via this intercostal access, the left atrium is opened. Into the two threaded bushings 34 and 46 of the spreader, rods for holding and manipulating, respectively, are screwed. With the aid of said rods engaging with the receptacles 24 and 26, the longitudinal edges 22 of the gap 20 are moved relative to one another in a peripheral direction against the elastic restoring force of the wall 16 in order to reduce the diameter of the retractor body 10. With this reduced diameter, the retractor body 10 is inserted into the opened left atrium by way of the guide rod until with its smaller distal edge 12, the retractor body is approximately positioned on the mitral valve. The axial measurements of the retractor body 10 are selected such that in this position, the proximal edge 14 of the retractor body 10 is located outside the atrium wall. In this position, the force introduced in peripheral direction via the rods and receptacles 24 and 26 is terminated so that due to its elasticity, and particularly due to its shape memory, the retractor body 10 spreads open such as the surrounding soft tissue allows. Both rods are then unscrewed from the respective threaded bushings 34 and 46. The fixing rod 54 is inserted into the thorax through a small incision laterally next to the intercostal access, and is connected to the first receptacle 34 by way of the threaded bushing 34. By means of the fixing rod 54 supported by the thorax wall, the retractor body 10 can now be put into the desired position, in which, for example, the distal edge 12 lines up with the annulus of the mitral valve. By screwing the fixing rod 54 into the threaded bushing 34 of the first receptacle 24 in different ways, the angle between the fixing rod 54 and the center axis of the retractor body 10 can further be adjusted such that the plane of the distal edge 12 matches the plane of the annulus of the mitral valve. Thus, the retractor body 10 is optimally adjusted in its position, and is fixed into place in this position by way of the fixing rod 54. In this position, the extracorporeal proximal end of the rod can be held in an angularly adjustable articulated arm and fixed into place.

In addition, threads can be fixed in the tissue of the heart, particularly in the area of the annulus of the mitral valve, and placed into the guides 52 of the retractor body 10 such that they extend from the distal guides 52 along the inner wall of the retractor body 10 to the proximal guides 52, and from there are guided out of the operating field and are held extracorporeally. Thus, in addition to the fixing rod 54, these threads secure the exact seating of the distal edge 12 of the retractor body 10 on the mitral valve. In this way, the retractor meets the objective of keeping view and access unobstructed for the surgeon over the entire circumference for the surgery on the mitral valve. After completion of the surgery, the spreader can be removed from the surgical site, wherefore the fixing rod 54 is first released from the first receptacle 24 in order to then reduce the diameter of the retractor body 10 again, and to remove the retractor body 10.

Figure 7:
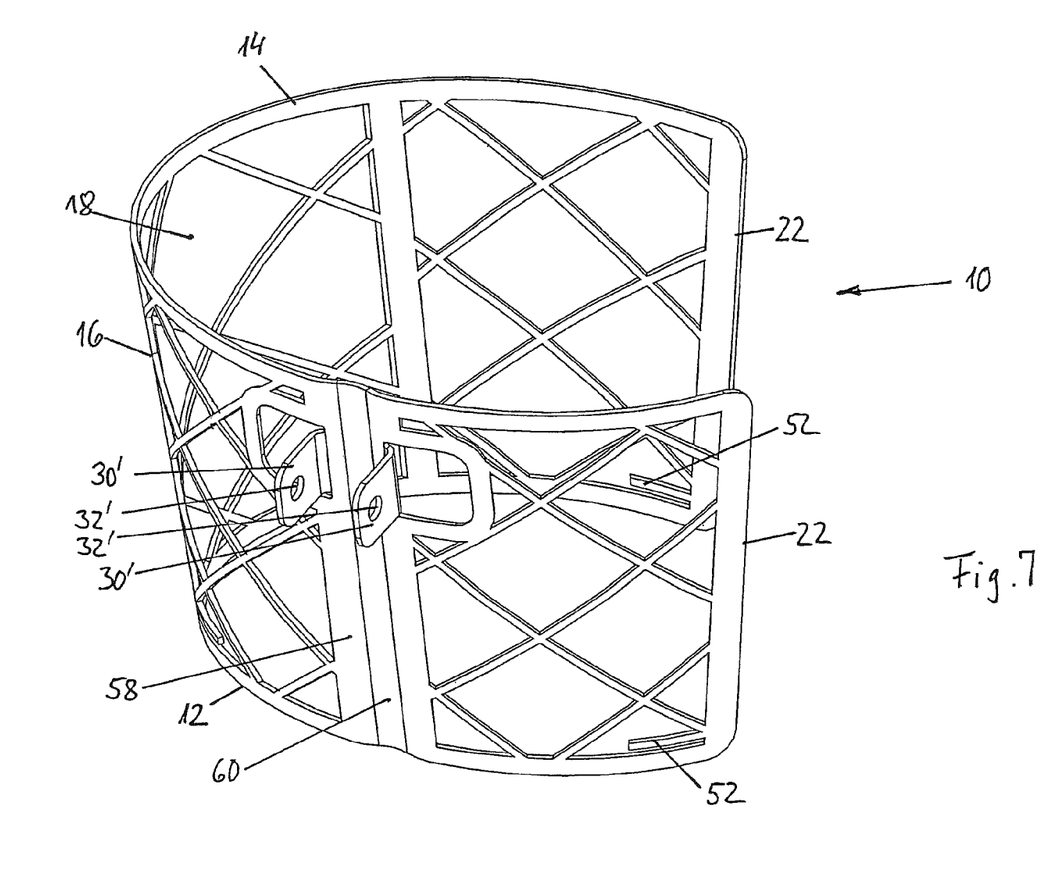
FIG. 7 is a perspective view of a second embodiment of the retractor body.
Figure 8:
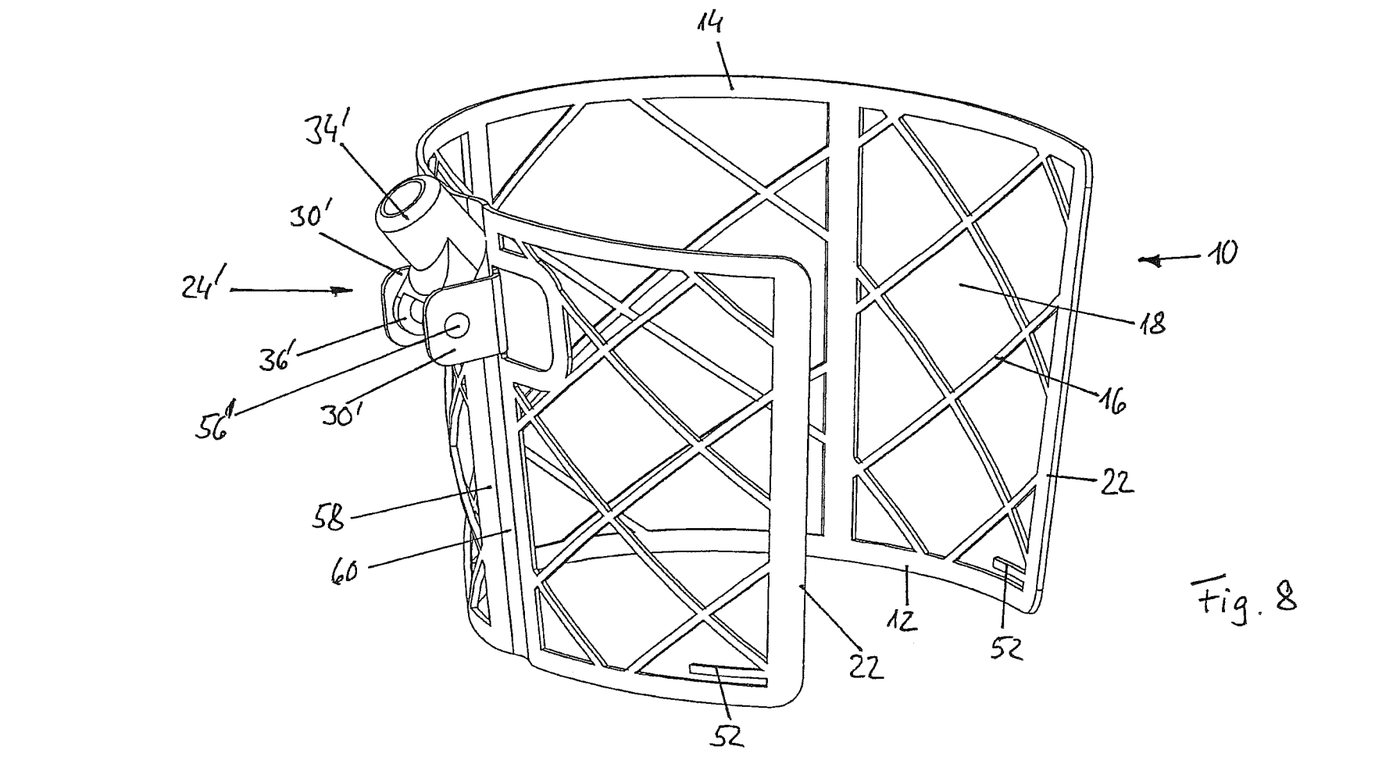
FIG. 8 is a perspective illustration of said second embodiment with the first receptacle.
Figure 9:
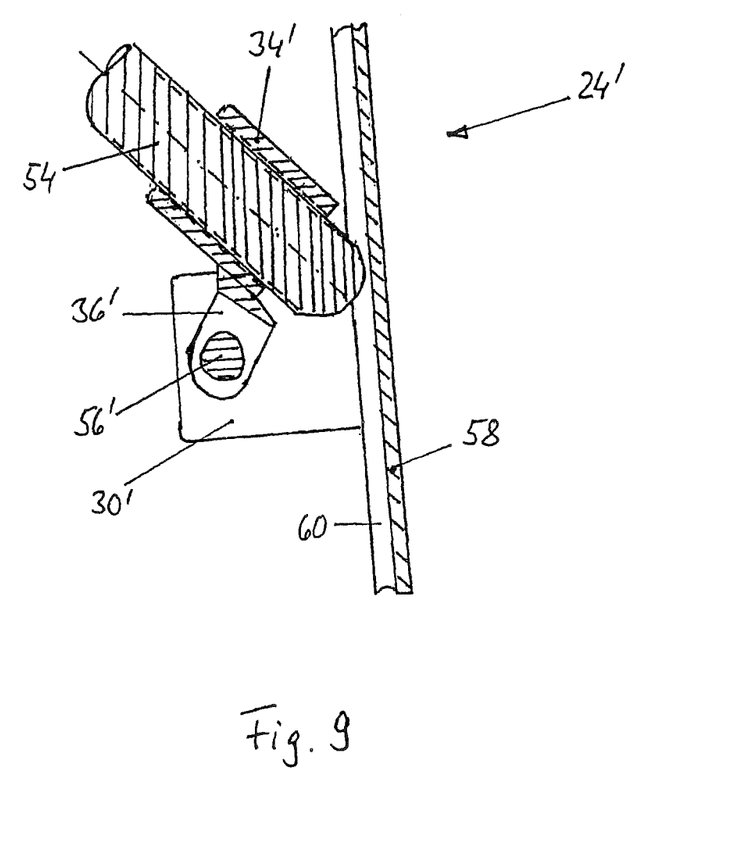
FIG. 9 shows a cross-section of the first receptacle with inserted fixing rod.

In FIGS. 7 to 9, a second embodiment of the spreader is illustrated. In this second embodiment, the retractor body 10 is essentially corresponding to the retractor body of the first exemplary embodiment of FIGS. 1 to 6, insofar as deviations are not described therebelow. To this extend, reference is made to the preceding description.

In this second embodiment, the spreader is provided with only one receptacle 24', into which the fixing rod 54 can be inserted. In this second embodiment, the first receptacle 24' is formed such that close to the proximal edge 14 of the retractor body 10, two flanges 30' are bent outwardly out of the wall 16 of the retractor body 10. The two flanges 30' project radially from the outer shell surface of the retractor body 10, and are parallel to one another in axial planes extending parallel to the center axis of the retractor body 10. Between the two flanges 30', an axially continuous bar 58 extends in a surface line of the retractor body 10. Centrally in the bar 58 on the external side thereof, a slightly recessed channel 60 extends in an axial direction. A threaded bushing 34' having a continuous threaded bore is placed between the flanges 30'. The threaded bushing 34' is pivotably mounted to the flanges 30', and thus to the retractor body 10, such that flanges 36' tangentially projecting from the threaded bushing 34' engage between the flanges 30', and an axle pin 56' is inserted into bearing bores 32' of the flanges 30' and 38' [sic] of the flanges 36' of the threaded bushing 34', which are aligned with one another. In this way, the threaded bushing 34' is pivotable around the axle pin 56' located tangentially to the retractor body 10.

With its distal end provided with the external screw thread, the fixing rod 54 is screwed into the threaded bushing 34'. The distal end of the fixing rod 54 protruding through the threaded bushing 34' is thereby supported by the bar 58, thus fixing the angle between the fixing rod 54 and the center axis of the retractor body 10. The distal end of the fixing rod 54 thereby engages in the channel 60 so that the fixing rod 54 is further secured against a movement of the retractor body 10 in a peripheral direction. If the fixing rod 54 is screwed further into the threaded bushing 34', the distal end of the fixing rod 54 is displaced on the bar 58 in a distal direction causing the fixing rod 54 to be pivoted around the axle pin 56' and the angle between the fixing rod 54 and the center axis of the retractor body 10 to be reduced.

In order to place the spreader in the second embodiment through the intercostal access into the atrium of the heart, the retractor body 10 is first extracorporeally pressed together by hand so that the axial gap 20 is closed and the longitudinal edges 22 overlap. In this way, the diameter of the retractor body 10 is reduced such that the retractor body 10 can be introduced into the opened atrium. In this compressed form, the overlapping longitudinal edges 22 of the retractor body 10 are grasped with the aid of a clamp or tongs, and are held adjacent to one another. By means of said clamp, that is, tongs, the retractor body 10 can then be inserted into the atrium of the heart until it rests with its distal end 12 on the annulus of the mitral valve. Thereafter, the clamp is removed so that the retractor body 10 spreads open elastically. Through an incision in the thorax wall laterally adjacent to the intercostal access, the fixing rod 54 is then inserted, and with its distal end is screwed into the threaded bushing 34' of the first receptacle 24'. The distal edge 12 of the retractor body 10 can thereby be positioned by means of the fixing rod 54. By screwing the fixing rod 54 into the threaded bushing 34' in different ways, the angle between the fixing rod 54 and the center axis of the retractor body 10 can be further adjusted until with its distal edge 12, the retractor body 10 is optimally positioned on the annulus of the mitral valve. In this position, the fixing rod 54 is fixed into place at its extracorporeal proximal end in order to maintain the retractor body 10 in the optimal position for the duration of the surgery.

LIST OF REFERENCE NUMERALS 10 retractor body
12 distal edge
14 proximal edge
16 wall
18 apertures
20 gap
22 longitudinal edges
24, 24' first receptacle
26 second receptacle
28 tab
30, 30' flanges
32, 32' bearing bores
34, 34' threaded bushing
36, 36' flanges
38, 38' bearing bores
40 tab
42 flanges
44 bearing apertures
46 threaded bushing
48 flanges
50 bearing apertures
52 guides
54 fixing rod
56, 56' axle pin
58 bar
60 channel

What is claimed:

1. A spreader for the atrium of the heart, comprising:
an axially continuous hollow retractor body with a wall and having a diameter that increases from a distal edge to a proximal edge, wherein the wall of the retractor body is an elastically deformable flat material, and wherein an axially continuous open gap is provided in a surface line of the retractor body so that the diameter of the retractor body can be reduced against its elasticity;
a receptacle arranged at the proximal edge of the retractor body;
a fixing rod pivotably connected to the retractor body;
wherein the fixing rod can releasably be inserted into the receptacle; and
wherein the wall includes a plurality of apertures arranged in a grid pattern;
a second receptacle arranged at the proximal edge of the retractor body; and
a guide rod inserted into the second receptacle and connected to the retractor body at a rigid angle.

2. The spreader according to claim 1, wherein the retractor body is of conical shape.

3. The spreader according to claim 1, wherein the wall of the retractor body is a metal sheet.

4. The spreader according to claim 3, wherein the wall of the retractor body is a shape memory metal.

5. The spreader according to claim 1, wherein a plurality of guides protrude from the distal edge of the retractor body and the proximal edge of the retractor body, respectively, into which threads can be placed in such a way that the threads are guided adjacent to an inside of the wall of the retractor body from the distal edge of the retractor body to the proximal edge of the retractor body.

6. The spreader according to claim 5, wherein the plurality of guides are hook-shaped open eyelets extending into an internal space of the retractor body.

7. A spreader for the atrium of the heart, comprising:
an axially continuous hollow retractor body with a wall and having a diameter that increases from a distal edge to a proximal edge, wherein the wall of the retractor body is an elastically deformable flat material arranged as a lattice, and wherein an axially continuous open gap is provided in a surface line of the retractor body so that the diameter of the retractor body can be reduced against its elasticity;
a receptacle arranged at the proximal edge of the retractor body;
a fixing rod pivotably connected to the retractor body; and
wherein the fixing rod can releasably be inserted into the receptacle;
a second receptacle arranged at the proximal edge of the retractor body; and a guide rod inserted into the second receptacle and connected to the retractor body at a rigid angle.

8. The spreader according to claim 7, wherein a plurality of guides protrude from the distal edge of the retractor body and the proximal edge of the retractor body, respectively, into which threads can be placed in such a way that the threads are guided adjacent to an inside of the wall of the retractor body from the distal edge of the retractor body to the proximal edge of the retractor body.

* * * * *